United States Patent [19]

Dirlikov et al.

[11] Patent Number: 4,709,059

[45] Date of Patent: Nov. 24, 1987

[54] PROCESS FOR SELECTIVE HALOGENATION OF PRIMARY HYDROXYL GROUPS

[75] Inventors: Stoil K. Dirlikov; Connie J. Schneider, both of Midland, Mich.

[73] Assignee: The Dow Chemical Company, Midland, Mich.

[21] Appl. No.: 764,287

[22] Filed: Aug. 12, 1985

[51] Int. Cl.$^4$ .................. C07D 317/16; C07C 31/18
[52] U.S. Cl. .................. 549/453; 549/423; 568/841; 568/676
[58] Field of Search ............... 549/453; 568/676, 841, 568/844, 614; 549/423, 417, 475, 476; 536/18.4, 122

[56] References Cited

U.S. PATENT DOCUMENTS 3,932,541 1/1976 Davis et al. .................. 568/844

Primary Examiner—Nicky Chan

[57] ABSTRACT

Epoxy compounds for use as epoxy resins are prepared from relatively inexpensive and renewable resources via a selective halogenation process. Primary pendant hydroxyl groups on straight carbon chain compounds with oxygen atoms pendant to each carbon are selectively halogenated with, for example, carbon tetrachloride. A scavenger agent, triphenylphosphine and pyridine, is used to complex the residual portion of reacted halogenating agent. One additional step with the halogenated intermediate yields epoxy compounds which, when cured, yield epoxy resins.

15 Claims, No Drawings

PROCESS FOR SELECTIVE HALOGENATION OF PRIMARY HYDROXYL GROUPS

BACKGROUND OF THE INVENTION

The present invention relates to compounds useful in the preparation of epoxy resins, and in particular to methods for preparing said compounds.

Epoxy resins are generally prepared by the reaction of epichlorohydrin with active hydrogen-bearing compounds, such as bisphenol A. Other methods for their preparation are the addition of glycidol to an acid chloride in the presence of triethylamine and Darzen's glycidic ester synthesis. More recently, epoxy acetal compounds with aliphatic main chains, have been prepared by reacting an unsaturated starting material with peracetic acid as described in U.S. Pat. No. 3,086,025, which is incorporated herein by reference. Unfortunately, the starting material is relatively expensive, thereby limiting the commercial application of the process.

Epoxy resins have been prepared from glycidyl ethers of cyclic ether anhydro hexitols as starting material via the epichlorohydrin process as is described in U.S. Pat. No. 3,041,300. However, these latter common epoxy components contain ether oxygen linkages in the backbone of the compound which are susceptible to oxidation and therefore provide poor weathering characteristics.

Accordingly, it would be highly desirable to provide a process for preparing an epoxy compound using an inexpensive and industrially available renewable resource which epoxy compound can be employed in order to provide an epoxy resin having good weathering characteristics.

SUMMARY OF THE INVENTION

In one aspect, the present invention is a process for selective halogenation of primary pendant hydroxyl groups in a straight carbon chain wherein each carbon in said chain is bonded to an oxygen atom pendant from said chain. The process comprises contacting the primary pendant hydroxyl groups with a functionally effective amount of halogenating agent and a complex enabling amount of scavenger agent, wherein said scavenger agent is capable of complexing with the remaining portion of unused halogenating agent.

In another aspect, the present invention relates to the incorporation of the aforementioned halogenating process in order to prepare epoxy compounds useful for preparing epoxy resins based on dianhydrohexitols and their derivatives.

The process of this invention provides the skilled artisan with a means of preparing a high yield of epoxy resin utilizing inexpensive and renewable resources. The process can be more economical than that method disclosed in U.S. Pat. No. 3,086,025.

DETAILED DESCRIPTION OF THE INVENTION

As used herein, the term "selective halogenation" is meant to include halogenation at the terminal or primary carbons of the straight chain compound wherein hydrolysis occurs and the primary pendant hydroxy groups are displaced with a halogen compound.

The straight carbon chain with primary pendant hydroxyl groups employed herein is most advantageously a polyol represented by the formula:

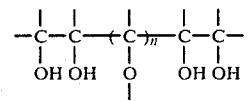

wherein n is 0 or greater but less than about 10, and the carbon in the backbone can be bonded to hydrogen or lower alkyl groups of from about 1 to about 3 carbon atoms. The oxygen atom(s) can be bonded to hydrogen or to a lower alkyl group of from about 1 to about 3 carbon atoms; the alkyl group can be bonded to an adjacent oxygen as well as form an epoxy acetal group. Examples of such polyols include pentitols, hexitols, heptitols, octitols, decitols, dodecitols and epoxy polyols.

By the term "halogenating agent" is meant a compound which will contain halogen and halogenate the primary carbons on the straight chain compound. Preferred halogenating agents are organic halogenating agents such as carbon tetrachloride, chloroform, carbon tetrabromide, and bromoform.

A functionally effective amount of halogenating agent is that amount which will selectively halogenate the primary carbons on the straight carbon chain. Typically, the effective amount will vary depending upon the number of reactive halogens there are in the halogenating agent. The most desirable amount of halogenating agent is that amount which displaces both primary pendant hydroxyl groups of the straight chain alkyl with halogen atoms. The amount generally can range from about 1 to about 1.5 moles of halogenating agent per primary pendant hydroxyl group. Typically, due to the fact that typical organic halogenating agents can serve as a suitable solvent for the reaction medium, the amount can be in large excess.

By the term "scavenger agent" is meant those compounds which are able to form a complex with the unused portion of the halogenating agent. Preferred scavenger agents comprise triphenyl phosphorous and aromatic heterocyclic nitrogen containing compounds. The more preferred scavenger agent comprises an admixture of triphenylphosphine and pyridine.

The relative amount of the triphenylphosphorous compound to the heterocyclic aromatic nitrogen containing compound is typically small due to the fact that, for example, the aromatic compound can serve as a suitable solvent for the triphenylphosphorous compound.

Examples of triphenylphosphorous compounds are triphenylphosphine, tritoluenephosphine, and the like.

Examples of aromatic heterocyclic nitrogen containing compounds are pyridine, pyrimidine, quinoline, isoquinoline, and the like.

Complex enabling amount of scavenger agent is that amount which will enable the residual portion of reacted halogenating agent to form a complex with said scavenger agent. This amount will vary depending upon the amount of halogenating agent that is necessary to effectively halogenate the aforementioned straight carbon chain compound. Typically, although the amount of the scavenger agent can vary, the amounts are preferably from about 2 to about 3 moles of scavenger agent per hydroxyl group.

The selective halogenating step of this invention is initiated by contacting the straight carbon chain containing pendant primary hydroxyl groups in a complex enabling amount of scavenger agent with a functionally effective amount of halogenating agent under cold temperatures. A suitable solvent is added and the mixture is removed, for example, by evaporation to yield the halogenated product which can be purified using techniques such as chromatography.

The epoxy compound can then be prepared by known methods. For example, the halogenated straight carbon chain can be contacted with sodium methylate in anhydrous alcohol under cold temperatures.

The epoxy compound so provided can be contacted with curing agents and cured to produce the epoxy resin. The epoxy compound is solidified by curing. In the curing of epoxy compounds the choice of curing agent can influence the cure rate, the exotherm and resultant properties of the finished product. Curing agents and their influence are known in the literature as, for example, in the book, *Handbook of Epoxy Resins,* and in *Chemical Reactions of Polymers,* Interscience Publishers, New York, pages 912–926, (1967) and in other reference works. Some of these influences are illustrated in Modern *Plastics Encyclopedia,* pages 33–34, (1982–1983).

Epoxy resins of this invention find a wide variety of uses in numerous applications. For example, stable dispersions are used as coatings (e.g., solution, high solids or powder coatings); fiber-reinforced laminates; advanced composites including aerospace, fiberglass reinforced plastics; tooling, casting and molding resins; bonding agents and adhesive agents in flooring, paving and exposed aggregate applications; and the like.

The following examples are presented to further illustrate but not limit the scope of the invention. All parts and percentages are given by weight unless otherwise indicated.

EXAMPLE 1

1,2:3,4:5,6-Tri-o-isopropylidene-d-mannitol is prepared by rapidly stirring with a mechanical stirrer, of 40 g of mannitol and 500 ml of anhydrous acetone in the presence of 4.0 ml of concentrated (18M) sulfuric acid as a catalyst for 24 hours in a 2 liter flask. The sulfuric acid is neutralized with about 6.8 g anhydrous sodium carbonate and the acetone is evaporated by vacuum distillation at about 30° C. The remaining yellowish oil is diluted with an equal volume of cold water in order to provide the crystalline product. The crystals are filtered, dried, and used without further purification.

3,4-O-Isopropylidene-d-mannitol is prepared by dissolving 10 g of previously provided crystalline product in 200 ml of aqueous 70 percent acetic acid, and the solution is heated at 40° C. for 1.5 hours. Then the solution is evaporated by vacuum distillation at 40° to 50° C. The residue is extracted with acetone, leaving some crystals undissolved. Evaporation of the acetone solution yields a syrup which completely crystallizes upon drying. Purified crystals are obtained after recrystallization from toluene.

1,6-Dichloro-1,6-dideoxy-3,4-o-isopropylidene-d-mannitol is obtained by gradually adding 100 ml of carbon tetrachloride to a solution of 11.1 g (5 mmole) of the aforementioned purified crystals and 26.3 g (10 mmole) of triphenylphosphine in 500 ml of anhydrous pyridine at 0° C. in a 500 ml flask. After holding the resulting solution at 5° C. for 18 hours, 100 ml of methanol is added, and the mixture is evaporated to a crystalline residue in quantitative yield. The residue is then chromatographically purified on a silica gel column. Elution first with chloroform and then with a 6/1 chloroform/acetone solution followed by a recrystallization from tolune/heptane, yields purified 1,6-dichloro-1,6-dideoxy-3,4-o-isopropylidene-d-mannitol crystals.

1,2:5,6-Dianhydro-3,4-o-isopropylidene-d-mannitol is prepared by carefully adding a solution of 2.49 g of sodium methylate in 20 ml of dry methyl alcohol at 0° C. to a solution of 5.29 g of the halogenated intermediate crystals in 30 ml of chloroform in a 250 ml flask. Thereafter, the solution is allowed to warm up to room temperature and kept thereat for 4 hours. More chloroform is then added, the mixture is washed with water, and the chloroform extract is dried with $MgSO_4$ and evaporated.

The product crystals are then ready to be used for preparation of epoxy resins without distillation.

EXAMPLE 2

1,2:5,6-dianhydro-3,4-o-isopropylidene-d-mannitol is cured with polyamides to prepare epoxy resins by mixing 0.465 g of product crystals with 0.72 g of a polyamide resin (amine value of 370–400 in 1:1 epoxy/amine group ratio) sold commercially as Versamid 140 polyamide resin by Henkel Corporation. The homogeneous mixture is cured as a thin layer between two (glass) microslides. The curing is carried out either at room temperature for 24 hours and then at 150° C. for 2 hours, or at room temperature for 7 days.

The halogenation of the 1,6 position of mannitol illustrates the selective halogenation process and the use of the process in formulating epoxy resins.

What is claimed is:

1. A process for selective halogenation of terminal carbon atoms bearing primary pendant hydroxyl groups in a polyol having a straight carbon chain wherein each carbon in said chain is bonded to an oxygen; said process comprising contacting said polyol with (a) a functionally effective amount of an organic halogenating agent which is a chlorinating agent or brominating agent and (b) a complex enabling amount of a scavenger agent which is able to form a complex with the remaining portion of unused halogenating agent under conditions sufficient to selectively replace the primary pendant hydroxyl groups of the polyol with halogens.

2. A process of claim 1 wherein said polyol is selected from the group consisting of pentitol, hexitol, heptitol, octitol, decitol and dodecitol.

3. A process of claim 1 wherein said straight carbon chain is an epoxy polyol.

4. A process of claim 1 wherein said halogenating agent is an organic chlorinating agent.

5. A process of claim 4 wherein said chlorinating agent is chloroform.

6. A process of claim 4 wherein said chlorinating agent is carbon tetrachloride.

7. A process of claim 1 wherein said halogenating agent is an organic brominating agent.

8. A process of claim 7 wherein said brominating agent is bromoform.

9. A process of claim 7 wherein said brominating agent is carbon tetrabromide.

10. A process of claim 1 wherein (1) said polyol is a pentitol, a hexitol, a heptitol, an octitol, a decitol or a dodecitol, and (2) said scavenger agent comprises a triphenyl phosphorous compound and an aromatic heterocyclic nitrogen compound.

11. A process of claim 10 wherein said triphenyl phosphorous compound is triphenylphosphine.

12. A process of claim 10 wherein said triphenyl phosphorous compound is tritoluenephosphine.

13. A process of claim 10 wherein said aromatic heterocyclic nitrogen compound is selected from the group consisting of pyrimidine, pyridine, quinoline and isoquinoline.

14. A process of claim 10 wherein said aromatic heterocyclic ring containing nitrogen compound is pyridine.

15. A process of claim 10 wherein said scavenger agent is triphenylphosphine and pyridine.

* * * * *